(12) United States Patent
Ancel

(10) Patent No.: US 6,620,944 B1
(45) Date of Patent: Sep. 16, 2003

(54) PROCESS FOR PREPARING PESTICIDAL INTERMEDIATES

(75) Inventor: Jean-Erick Ancel, Saint-Genis-Laval (FR)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 09/890,653

(22) PCT Filed: Feb. 1, 2000

(86) PCT No.: PCT/EP00/01101
§ 371 (c)(1),
(2), (4) Date: Nov. 1, 2001

(87) PCT Pub. No.: WO00/46210
PCT Pub. Date: Aug. 10, 2000

(30) Foreign Application Priority Data

Feb. 4, 1999 (FR) .............................. 99 01469

(51) Int. Cl.$^7$ ............................ C07D 231/38
(52) U.S. Cl. .................. 548/371.7; 548/377.1
(58) Field of Search ................ 548/371, 372, 548/375, 377.1

(56) References Cited

U.S. PATENT DOCUMENTS 5,232,940 A    8/1993    Hatton et al.

FOREIGN PATENT DOCUMENTS

| EP | 0234119 A | 9/1987 | |
|----|-----------|--------|--|
| EP | 0295117 A | 12/1988 | |
| EP | 0295117 | * 12/1988 | ......... C07D/231/44 |
| WO | 94/13643 A | 6/1994 | |
| WO | 97/32843 A | 9/1997 | |
| WO | 98/39302 A | 9/1998 | |

* cited by examiner

Primary Examiner—Alan L. Rotman
Assistant Examiner—Janet L Coppins
(74) Attorney, Agent, or Firm—Burns, Doane, Swecker & Mathis, L.L.P.

(57) ABSTRACT

A process for preparing pesticides or pesticidal intermediates, particularly 5-amino-1 aryl-3-cyanopyrazoles, having the formula

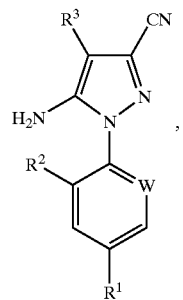

(I)

said process comprising reacting a compound having the formula

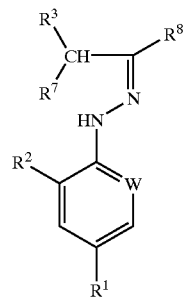

(II)

with a cyanide salt.

17 Claims, No Drawings

PROCESS FOR PREPARING PESTICIDAL INTERMEDIATES

This invention relates to novel processes for preparing, pesticides or pesticidal intermediates (particularly 5-amino-1-aryl-3-cyanopyrazole derivatives).

European Patent Publication Nos. 0295117 and 0234119 describe the preparation of pesticidally active phenylpyrazole compounds and of 5-amino-1-aryl-3-cyanopyrazole intermediate compounds used in their synthesis.

Various methods for preparing these compounds are known. The present invention seeks to provide improved or more economical methods for the preparation of pesticides and the intermediate compounds useful in preparing them.

It is a first object of the present invention to provide a convenient process for preparing pesticidally active phenylpyrazole compounds or 5-amino-1-aryl-3-cyanopyrazole pesticidal intermediates, which are obtained in high yield and high purity.

It is a second object of the present invention to provide a convenient process for preparing pesticidally active phenylpyrazole compounds or 5-amino-1-aryl-3-cyanopyrazole pesticidal intermediates, which proceeds without the need for a diazotisation step and hence avoids problems such as hazards known to occur for such reactions.

It is a third object of the present invention to provide a process for preparing pesticidally active phenylpyrazole compounds or 5-amino-1-aryl-3-cyanopyrazole pesticidal intermediates, which is simple to perform and uses less expensive starting materials than known methods.

It is a still further object of the present invention to provide novel intermediates in the manufacture of pesticidally active compounds.

These and other objects of the invention will become apparent from the following description, and are achieved in whole or in part by the present invention.

The present invention accordingly provides a process (A) for the preparation of a compound of formula (I):

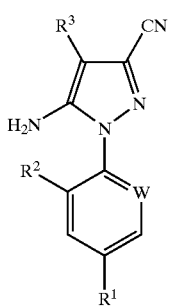

(I)

wherein W represents nitrogen or —CR$^4$;

$R^1$ represents halogen, haloalkyl (preferably trifluoromethyl), haloalkoxy (preferably trifluoromethoxy), $R^5S(O)_n$—, or —SF$_5$;

$R^2$ represents hydrogen or halogen (for example chlorine or bromine);

$R^3$ represents hydrogen or $R^6S(O)_m$—;

$R^4$ represents halogen (for example chlorine or bromine);

$R^5$ and $R^6$ represent alkyl or haloalkyl; and m and n represent 0, 1 or 2; which process comprises the reaction of a compound of formula (II):

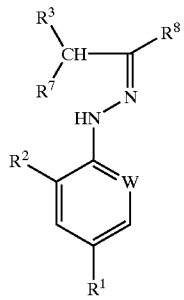

(II)

wherein $R^1$, $R^2$, $R^3$ and W are as hereinbefore defined, $R^7$ represents a leaving group (preferably chlorine or bromine) and $R^8$ represents chlorine or bromine (preferably $R^7$ and $R^8$ each represent chlorine), with a cyanide salt. The reaction proceeds via dicyano intermediates of formula (III):

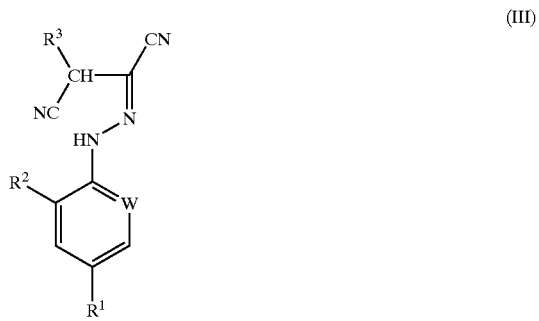

(III)

wherein $R^1$, $R^2$, $R^3$ and W are as hereinbefore defined, which generally cyclise under the conditions of the reaction, thus providing a simple and convenient process. Optionally the intermediates of formula (III) may be cyclised in the presence of base according to known methods. Compounds of formula (II) and (III) may exist as a mixture of syn and anti isomers.

Unless otherwise specified in the present specification 'alkyl' means straight- or branched-chain alkyl having from one to six carbon atoms (preferably one to three). Unless otherwise specified 'haloalkyl' and 'haloalkoxy' are straight- or branched-chain alkyl or alkoxy respectively having from one to six carbon atoms (preferably one to three) substituted by one or more halogen atoms selected from fluorine, chlorine or bromine.

Suitable cyanide salts for the above reaction to form compounds of formula (I) include alkali metal cyanides such as potassium, sodium or lithium cyanide, alkaline earth metal cyanides or ammonium cyanide. Potassium cyanide or sodium cyanide are preferred. The reaction is generally conducted in a solvent. Solvents suitable for use include nitriles such as acetonitrile, amides such as N-methylpyrrolidinone, sulphoxides such as dimethylsulphoxide, ethers such as tetrahydrofuran or alcohols such as ethanol. Water may be employed as a co-solvent. The reaction temperature is generally from about −20° C. to the reflux temperature of the solvent, and preferably from about 0° C. to about 20° C.

Generally from two to 5 molar equivalents of cyanide and preferably from about two to about three equivalents are employed.

In formulae (I), (II) and (III) and in the formulae depicted hereinafter, preferred values of the symbols are as follows:

$R^1$ represents haloalkyl (preferably trifluoromethyl), haloalkoxy (preferably trifluoromethoxy) or —$SF_5$;

W represents —$CR^4$;

$R^2$ and $R^4$ represent halogen (preferably chlorine);

$R^3$ represents a hydrogen atom, or $R^6S(O)_m$—; wherein $R^6$ represents optionally halogenated methyl or ethyl (preferably trifluoromethyl); and $R^7$ and $R^8$ represent chlorine.

Particularly preferred compounds of formula (I) include:

5-amino-3-cyano-1-(2,6-dichloro-4-trifluoromethylphenyl) pyrazole;

5-amino-3-cyano-1-(2,6-dichloro-4-trifluoromethylphenyl)-4-trifluoromethylthiopyrazole;

5-amino-3-cyano-1-(2,6-dichloro-4-trifluoromethylphenyl)-4-trifluoromethylsulphinylpyrazole; and 5-amino-3-cyano-1-(2,6-dichloro-4-trifluoromethylphenyl)-4-ethylsulphinylpyrazole.

The process is particularly useful for preparing compounds in which $R^3$ represents hydrogen, and most preferably for 5-amino-3-cyano-1-(2,6-dichloro-4-trifluoromethylphenyl)pyrazole.

In formulae (II) and (III) and in the formulae depicted hereinafter, the most preferred values of the symbols are as follows:

$R^1$ represents trifluoromethyl;

W represents —$CR^4$;

$R^2$, $R^4$, $R^7$ and $R^8$ represent chlorine; and $R^3$ represents hydrogen.

According to a further feature of the present invention the above process (A) can be combined with additional process steps (B) and (C) as defined hereinbelow.

Process step (B); comprises the reaction of a compound of formula (IV):

(IV)

wherein $R^1$, $R^2$, $R^3$, $p^7$ and W are as hereinbefore defined, with a chlorinating or brominating agent; to give a compound of formula (II) wherein $R^1$, $R^2$, $R^3$, $R^7$, $R^8$ and W are as hereinbefore defined.

Suitable chlorinating agents are thionyl chloride, phosphoryl chloride, phosphorus trichloride, phosphorus pentachloride or a mixture of triphenylphosphine and carbon tetrachloride. Brominating agents which may be used include thionyl bromide, phosphoryl bromide or a mixture of triphenylphosphine and carbon tetrabromide. Preferably the process is performed using a chlorinating agent. A preferred chlorinating agent is phosphoryl chloride.

Solvents which may be used include ethers, aromatic hydrocarbons such as toluene, aromatic halogenated hydrocarbons such as chlorobenzene, or halogenated hydrocarbons such as dichloroethane.

The reaction temperature is generally from 0° C. to 120° C., preferably from 70° C. to 90° C.

Process step (C) comprises the reaction of an arylhydrazine compound of formula (V):

(V)

wherein $R^1$, $R^2$ and W are as hereinbefore defined; with a compound of formula (VI):

$R^3R^7CHCOR^9$ (VI)

wherein $R^3$ and $R^7$ are as defined above, and $R^9$ represents a leaving group preferably a chlorine or bromine atom (generally both $R^7$ and $R^9$ represent a chlorine atom); to give a compound of formula (IV) as defined above. The reaction to obtain compounds of formula (IV) is generally performed in a solvent such as halogenated hydrocarbons for example dichloromethane, ethers for example tetrahydrofuran or dioxan, or N,N-dialkylamides for example N,N-dimethylformamamide, and at a temperature of from –20° to 50° C., preferably from 0 to 20° C.

The above combination of process step (A), preceded by process step (B), preceded by process step (C), represents in certain aspects an improvement over the prior art.

Compounds of formula (II) and (IV) above are novel and therefore constitute a further feature of the present invention.

Where $R^3$ is other than hydrogen, compounds of formula (III) are novel.

Compounds of formula (VI) are known.

The intermediate 5-amino-1-aryl-3-cyanopyrazole compounds of formula (I) obtained by the process (A) of the invention wherein $R^3$ represents hydrogen, may be used in the preparation of pesticidally active phenylpyrazole derivatives of formula (VII) according to the following reaction scheme:

(I) → 1. $R^6SCl$ 2. oxidise → (VII)

wherein the symbols used above are as hereinbefore defined.

The following non-limiting examples illustrate the invention. NMR spectra are recorded using deuterochloroform as solvent.

EXAMPLE 1

Preparation of 5-amino-1-(2,6-dichloro-4-trifluoromethylphenyl)-3-cyanopyrazole

A solution of N'-(2,6-dichloro-4-trifluoromethylphenyl)-chloroacetohydrazonoyl chloride (1.1 g) in ethanol (6 ml)

was added during 25 minutes to a stirred solution of sodium cyanide (0.475 g) in ethanol (6 ml) and water (6 ml). The temperature rose to 32° C. After 15 minutes an addition of ethanol (4.5 ml) and water (3 ml) was made and stirred for 15 minutes at 20° C. A further addition of water (3 ml) was made and the mixture filtered. The residue was dissolved in ethanol, concentrated and purified by chromatography on silica gel eluting with dichloromethane to give the title compound (0.55 g), obtained in 53% yield.

EXAMPLE 2

Preparation of N'-(2,6-dichloro-4-trifluoromethylphenyl)-chloroacetohydrazonoyl chloride Phosphoryl chloride (500 microlitres, 1.7 equivalents) was added in one portion to a stirred solution of N'-(2,6-dichloro-4-trifluoromethylphenyl)-chloroacetohydrazide (1.0 g, 3.11 mmol) in toluene (20 ml) and heated at 70° C. under an argon atmosphere for 20 hours. The cooled mixture was evaporated and the residue extracted with cyclohexane. The extracts were combined and evaporated to give the title compound (0.971 g) as an orange oil, NMR 4.4(s,2H), 7.55(s,2H), 7.7(s,1H). The yield was 90%.

EXAMPLE 3

Preparation of N'-(2,6-dichloro-4-trifluoromethylphenyl)-chloroacetohydrazide

A solution of chloroacetyl chloride (2.3 ml, 1.08 equivalents) in anhydrous dichloromethane (30 ml) was added during 30 minutes to a stirred solution of 2,6-dichloro-4-trifluoromethylphenylhydrazine (6.1 g, 24.89 mmol) in anhydrous dichloromethane (60 ml) maintaining between 5 and 12° C. under an argon atmosphere. The mixture was then stirred for 5–12 hours at 20° C. A solution of sodium hydroxide (11.2 ml of 10%) and dichloromethane were added and the organic phase washed (water), dried (magnesium sulphate) and evaporated to give the title compound (7.25 g) as a white solid, NMR 4.05(s,2H), 6.77(s, 1H), 7.47(s,2H), 8.6(s,1H). The yield was 91%.

What is claimed is:

1. A process for the preparation of a compound having the formula:

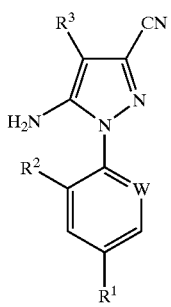

(I)

wherein:
W is —CR$^4$;
R$^1$ is halogen, haloalkyl, haloalkoxy, R$^5$S(O)$_n$— or —SF$_5$;
R$^2$ is hydrogen or halogen;
R$^3$ is hydrogen or R$^6$S(O)$_m$—;
R$^4$ is halogen;
each of R$^5$ and R$^6$ is alkyl or haloalkyl; and
each of m and n is 0, 1 or 2;
said process comprising:
(a) reacting a compound having the formula:

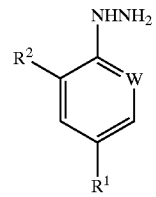

(V)

wherein R$^1$, R$^2$ and W are as defined above, with a compound having the formula:

R$^3$R$^7$CHCOR$^9$  (VI)

wherein R$^3$ is as defined above and each of R$^7$ and R$^9$ is a leaving group, to afford the corresponding compound having the formula:

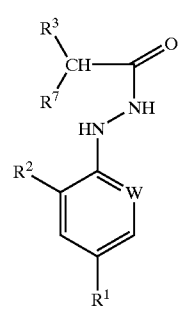

(IV)

wherein R$^1$, R$^2$, R$^3$, R$^7$ and W are as defined above;
(b) reacting the resultant compound of formula (IV) with a chlorinating or brominating agent, to afford the corresponding compound having the formula:

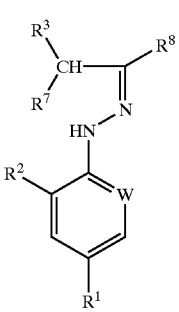

(II)

wherein R$^1$, R$^2$, R$^3$, R$^7$ and W are as defined above and R$^8$ is chlorine or bromine; and
(c) reacting the resultant compound of formula (II) with a cyanide salt.

2. A process according to claim 1, wherein the compound of formula (IV) is reacted in step (b) with a chlorinating agent selected from the group consisting of thionyl chloride, phosphoryl chloride, phosphorus trichloride, phosphorus pentachloride, and a mixture of triphenylphosphine and carbon tetrachloride.

3. A process according to claim 1, wherein the cyanide salt in step (c) is an alkali metal cyanide, an alkaline earth metal cyanide or ammonium cyanide.

4. A process according to claim 3, wherein the cyanide salt is potassium cyanide or sodium cyanide.

5. A process according to claim 1, wherein step (c) is conducted in a solvent selected from the group consisting of nitrites, amides, sulfoxides, ethers and alcohols, optionally in the presence of water.

6. A process according to claim 5, wherein the solvent comprises acetonitrile, N-methylpyrrolidinone, dimethylsulfoxide, tetrahydrofuran or ethanol.

7. A process according to claim 1, wherein in step (c) from 2 to 5 molar equivalents of cyanide are employed.

8. A process according to claim 1, wherein in step (c) the reaction temperature is from about −20° C. to the reflux temperature of the solvent.

9. A process according to claim 8, wherein in step (c) the reaction temperature is from about 0° C. to about 20° C.

10. A process according to claim 1, wherein $R^7$ is chlorine or bromine.

11. A process according to claim 3, wherein $R^7$ is chlorine or bromine.

12. A process according to claim 7, wherein $R^7$ is chlorine or bromine.

13. A process according to claim 1, wherein:

$R^1$ is trifluoromethyl, trifluoromethoxy or —SF$_5$;

each of $R^2$ and $R^4$ is chlorine or bromine;

$R^3$ is hydrogen or $R^6S(O)_m$—;

$R^6$ is optionally halogenated methyl or ethyl; and each of $R^7$ and $R^8$ is chlorine.

14. A process according to claim 13, wherein:

$R^1$ is trifluoromethyl;

each of $R^2$, $R^4$, $R^7$ and $R^8$ is chlorine; and $R^3$ is hydrogen.

15. A process according to claim 1, wherein the compound of formula (I) is:

5-amino-3-cyano-1-(2,6-dichloro-4-trifluoromethylphenyl) pyrazole;
5-amino-3-cyano-1-(2,6-dichloro-4-trifluoromethylphenyl)-4-trifluoromethylthiopyrazole;
5-amino-3-cyano-1-(2,6-dichloro-4-trifluoromethylphenyl)-4-trifluoromethylsulfinylpyrazole; or
5-amino-3-cyano-1-(2,6-dichloro-4-trifluoromethylphenyl)-4-ethylsulfinylpyrazole.

16. A process according to claim 1, wherein in step (c) the intermediate having the formula:

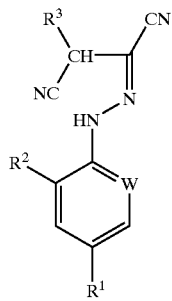

(III)

wherein $R^1$, $R^2$, $R^3$ and W are as defined in claim 1, which is formed in the course of the reaction, cyclizes under the conditions of the reaction to afford the corresponding compound of formula (I).

17. A process according to claim 1, wherein in step (c) the intermediate having the formula:

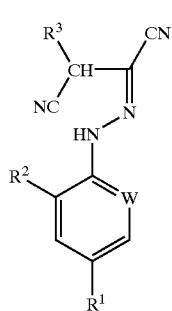

(III)

wherein $R^1$, $R^2$, $R^3$ and W are as defined in claim 1, which is formed in the course of the reaction, is cyclized in the presence of base to afford the corresponding compound of formula (I).

* * * * *